US012318207B2

(12) United States Patent
Govari et al.

(10) Patent No.: US 12,318,207 B2
(45) Date of Patent: Jun. 3, 2025

(54) TRANSIENT EVENT IDENTIFICATION

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 784 days.

(21) Appl. No.: 17/532,835

(22) Filed: Nov. 22, 2021

(65) Prior Publication Data

US 2023/0157616 A1    May 25, 2023

(51) Int. Cl.
*A61B 5/349* (2021.01)
*A61B 5/00* (2006.01)
*A61B 5/287* (2021.01)
*A61B 5/339* (2021.01)

(52) U.S. Cl.
CPC ............. *A61B 5/349* (2021.01); *A61B 5/287* (2021.01); *A61B 5/339* (2021.01); *A61B 5/6858* (2013.01); *A61B 2562/0209* (2013.01)

(58) Field of Classification Search
CPC ......... A61B 5/349; A61B 5/353; A61B 5/355; A61B 5/357; A61B 5/358; A61B 5/36; A61B 5/339; A61B 5/343; A61B 5/287; A61B 5/274; A61B 5/276; A61B 5/6858; A61B 2562/0209; A61B 5/24; A61B 5/25; A61B 5/283; A61B 5/291; A61B 5/296; A61B 5/053
See application file for complete search history.

(56) References Cited

U.S. PATENT DOCUMENTS

| 5,391,199 | A  | 2/1995  | Ben-Haim |
| 6,239,724 | B1 | 5/2001  | Doron et al. |
| 6,332,089 | B1 | 12/2001 | Acker et al. |
| 6,484,118 | B1 | 11/2002 | Govari |
| 6,618,612 | B1 | 9/2003  | Acker et al. |
| 6,690,963 | B2 | 2/2004  | Ben-Haim et al. |
| 7,756,576 | B2 | 7/2010  | Levin |
| 7,848,787 | B2 | 12/2010 | Osadchy |

(Continued)

FOREIGN PATENT DOCUMENTS

| WO | WO 1996/005768 A1 | 2/1996 |
| WO | 2014100631 A1 | 6/2014 |

OTHER PUBLICATIONS

Extended European Search Report dated Mar. 29, 2023, from corresponding European Application No. 22208492.3.

*Primary Examiner* — Eric F Winakur
*Assistant Examiner* — Noah M Healy

(57) ABSTRACT

In one embodiment, a medical system includes a catheter configured to be inserted into a chamber of a heart of a living subject, and including catheter electrodes configured to contact tissue at respective locations within the chamber of the heart, a display, and a processing circuitry configured to receive respective signals from the catheter captured by respective ones of the electrodes, assess conformity of each of the respective signals to at least one signal characteristic, find a given one of the signals of a given one of the electrodes not conforming to the at least one signal characteristic for a given time period, and render to the display an indication that the given signal of the given electrode does not conform to the at least one signal characteristic for the given time period.

18 Claims, 4 Drawing Sheets

(56) References Cited

U.S. PATENT DOCUMENTS

| | | |
|---|---|---|
| 7,869,865 B2 | 1/2011 | Govari |
| 8,721,594 B2 | 5/2014 | Zacharias |
| 10,940,039 B2 | 3/2021 | Banko |
| 11,918,383 B2* | 3/2024 | Palti ........................ A61B 5/287 |
| 2002/0065455 A1 | 5/2002 | Ben-Haim et al. |
| 2003/0120150 A1 | 6/2003 | Govari |
| 2004/0068178 A1 | 4/2004 | Govari |
| 2014/0257172 A1 | 9/2014 | Yalamanchili |
| 2015/0254893 A1* | 9/2015 | Laughner ............... A61B 5/341 |
| | | 345/422 |
| 2018/0242868 A1* | 8/2018 | Cohen .................... A61B 5/062 |
| 2021/0100612 A1 | 4/2021 | Baron et al. |
| 2022/0202482 A1* | 6/2022 | Doron .................... A61B 90/39 |
| 2022/0287615 A1* | 9/2022 | Lou ........................ A61B 5/339 |

* cited by examiner

TRANSIENT EVENT IDENTIFICATION

FIELD OF THE INVENTION

The present invention relates to medical systems, and in particular, but not exclusively, to catheter devices.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser, pulsed field, and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied between the tip electrode(s) of the ablating catheter, and the reference electrode, flowing through the media between the electrodes it, i.e., blood and tissue. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

SUMMARY

There is provided in accordance with an embodiment of the present disclosure, a medical system, including a catheter configured to be inserted into a chamber of a heart of a living subject, and including catheter electrodes configured to contact tissue at respective locations within the chamber of the heart, a display, and a processing circuitry configured to receive respective signals from the catheter captured by respective ones of the electrodes, assess conformity of each of the respective signals to at least one signal characteristic, find a given one of the signals of a given one of the electrodes not conforming to the at least one signal characteristic for a given time period, and render to the display an indication that the given signal of the given electrode does not conform to the at least one signal characteristic for the given time period.

Further in accordance with an embodiment of the present disclosure the processing circuitry is configured to render to the display a representation of the catheter with the indication that the given signal of the given electrode does not conform to the at least one signal characteristic for the given time period, wherein the indication is linked to the given electrode on the representation of the catheter.

Still further in accordance with an embodiment of the present disclosure the processing circuitry is configured to render to the display a representation of the catheter with the indication that the given signal of the given electrode does not conform to the at least one signal characteristic for the given time period, wherein the indication is disposed on the given electrode on the representation of the catheter.

Additionally in accordance with an embodiment of the present disclosure the processing circuitry is configured to render to the display the indication disposed on the given electrode on the representation of the catheter for a given time interval, remove the indication from the given electrode on the representation of the catheter, and repeat rendering to the display of the indication disposed on the given electrode on the representation of the catheter responsively to finding that the given signal of the given electrode does not conform to the at least one signal characteristic for a subsequent time period.

Moreover, in accordance with an embodiment of the present disclosure the processing circuitry is configured to render to the display the indication disposed on the given electrode on the representation of the catheter so that the indication repeatedly flashes on and off responsively to multiple detections of the given signal of the given electrode not conforming to the at least one signal characteristic for respective subsequent time periods.

Further in accordance with an embodiment of the present disclosure the respective subsequent time periods correspond to respective windows of interest of respective cardiac cycles.

Still further in accordance with an embodiment of the present disclosure the processing circuitry is configured to receive a user input requesting display of an electrogram captured by the given electrode, and render to the display the electrogram captured by the given electrode.

Additionally in accordance with an embodiment of the present disclosure the given time period is equal to a window of interest in one cardiac cycle.

Moreover, in accordance with an embodiment of the present disclosure the given time period is equal to multiple windows of interest of respective cardiac cycles.

Further in accordance with an embodiment of the present disclosure the processing circuitry is configured to save the given signal to a memory for future rendering to the display.

There is also provided in accordance with another embodiment of the present disclosure a medical method, including receiving respective signals from a catheter inserted into a chamber of a heart of a living subject captured by respective electrodes of the catheter contacting tissue at respective locations within the chamber of the heart, assessing conformity of each of the respective signals to at least one signal characteristic, finding a given one of the signals of a given one of the electrodes not conforming to the at least one signal characteristic for a given time period, and rendering to the display an indication that the given signal of the given electrode does not conform to the at least one signal characteristic for the given time period.

Still further in accordance with an embodiment of the present disclosure the rendering includes rendering to the display a representation of the catheter with the indication that the given signal of the given electrode does not conform to the at least one signal characteristic for the given time period, wherein the indication is linked to the given electrode on the representation of the catheter.

Additionally in accordance with an embodiment of the present disclosure the rendering includes rendering to the display a representation of the catheter with the indication that the given signal of the given electrode does not conform to the at least one signal characteristic for the given time period, wherein the indication is disposed on the given electrode on the representation of the catheter.

Moreover in accordance with an embodiment of the present disclosure the rendering includes rendering to the display the indication disposed on the given electrode on the representation of the catheter for a given time interval, the method further including removing the indication from the given electrode on the representation of the catheter, and repeating rendering to the display of the indication disposed on the given electrode on the representation of the catheter responsively to finding that the given signal of the given electrode does not conform to the at least one signal characteristic for a subsequent time period.

Further in accordance with an embodiment of the present disclosure the rendering includes rendering to the display the indication disposed on the given electrode on the representation of the catheter so that the indication repeatedly flashes on and off responsively to multiple detections of the given signal of the given electrode not conforming to the at least one signal characteristic for respective subsequent time periods.

Still further in accordance with an embodiment of the present disclosure the respective subsequent time periods correspond to respective windows of interest of respective cardiac cycles.

Additionally in accordance with an embodiment of the present disclosure, the method includes receiving a user input requesting display of an electrogram captured by the given electrode, and wherein the rendering includes rendering to the display the electrogram captured by the given electrode.

Moreover, in accordance with an embodiment of the present disclosure the given time period is equal to a window of interest in one cardiac cycle.

Further in accordance with an embodiment of the present disclosure the given time period is equal to multiple windows of interest of respective cardiac cycles.

Still further in accordance with an embodiment of the present disclosure, the method includes saving the given signal to a memory for future rendering to the display.

There is also provided in accordance with still another embodiment of the present disclosure a software product, including a non-transient computer-readable medium in which program instructions are stored, which instructions, when read by a central processing unit (CPU), cause the CPU to receive respective signals from a catheter inserted into a chamber of a heart of a living subject captured by respective electrodes of the catheter contacting tissue at respective locations within the chamber of the heart, assess conformity of each of the respective signals to at least one signal characteristic, find a given one of the signals of a given one of the electrodes not conforming to the at least one signal characteristic for a given time period, and render to the display an indication that the given signal of the given electrode does not conform to the at least one signal characteristic for the given time period.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
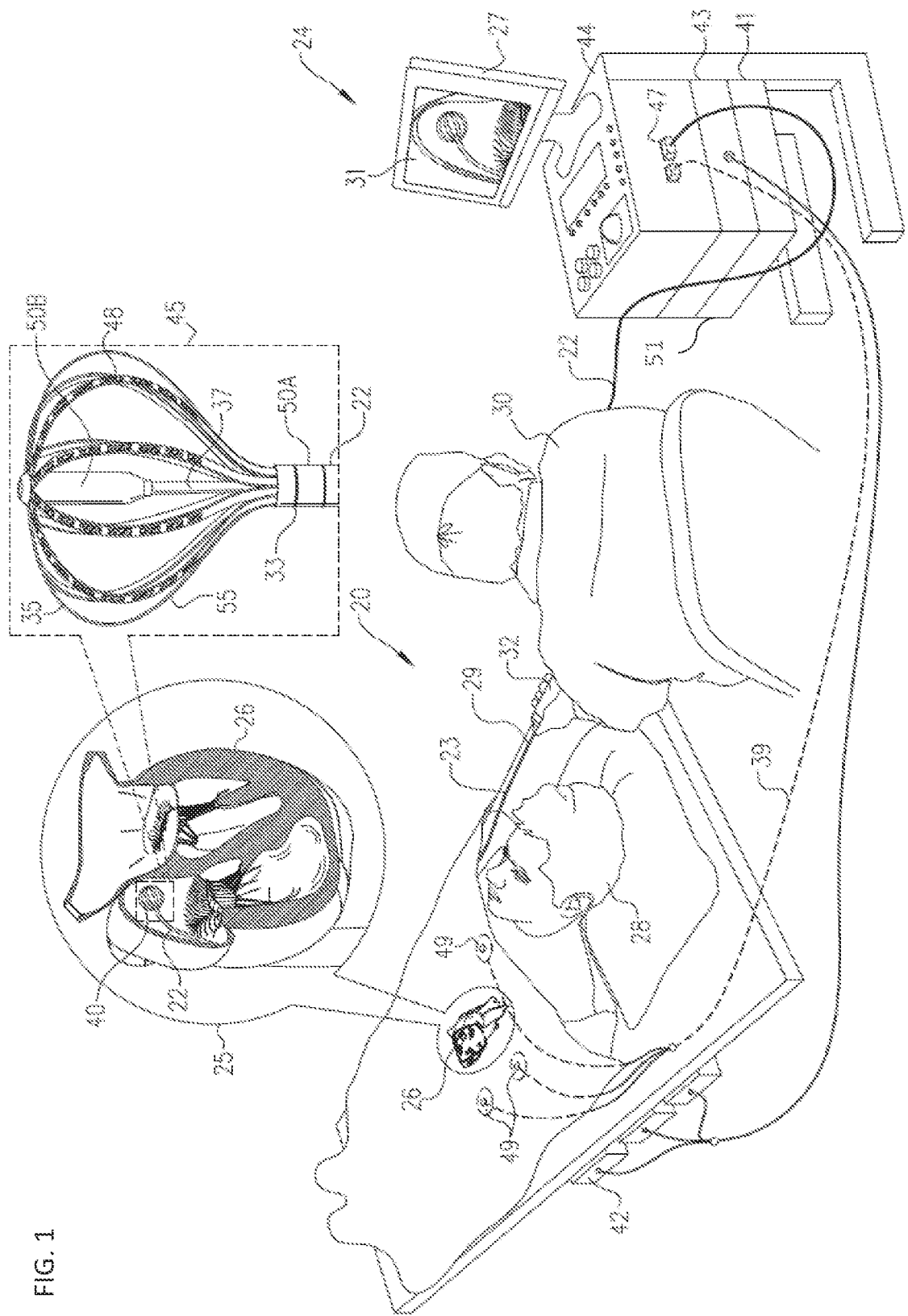
FIG. 1 is a schematic, pictorial illustration of a catheter tracking system constructed and operative in accordance with an embodiment of the present invention.

During the mapping process, unexpected signals that do not fit into the category of expected mapping signals may be captured by catheter electrodes. These unexpected signals may be due to noise and/or physiological factors leading to complex signals including late activations, or double/multiple activations per cardiac cycle. Although these unexpected signals may be interesting for the physician, these unexpected signals are difficult to treat algorithmically (and may cause errors in the mapping process) and are generally filtered out as non-mapping signals and ignored by the mapping algorithm. Nevertheless, complex signals may be the most interesting signals for the physician and may indicate a heart defect which should be treated. However, as mentioned above these complex signals are generally excluded from the mapping process.

Embodiments of the invention use the signals filtered out as non-mapping signals and provide respective indications to the physician that such non-mapping signals exist. The physician may then select the non-mapping signals for viewing to determine if the signals are physiologically relevant.

In some embodiments, a mapping system assesses conformity of each signal to one or more signal characteristics for a given time period (e.g., for a window of interest of each signal in one or more cardiac cycles). The signals for a given time period may also be referred to as signal segments for the given time period. The signal characteristics for classifying a signal segment (for a given time period) as a valid mapping signal may include a signal having a single activation early enough in the cardiac cycle. Signal segments with late, double, multiple, or unclear activations may be excluded as not conforming with the signal characteristics. In some embodiments, peaks above a given threshold are considered as possible activations, whereas peaks below the given threshold are not considered as possible activations for determining how many activations a signal segment has in the window of interest and how late the activations are in the window of interest. The activation time may be defined by the steepest negative slope of a candidate peak or any other suitable criteria. The definition of "early enough" in the cardiac cycle, the window of interest, and the given threshold for identifying peaks may be implementation specific and/or physician defined. In some embodiments, the physician defines the "window of interest". For example, in atrial procedures, the "window of interest" may be defined by setting limits around the P wave, which may be identified based on the R peak of the QRS complex. The definition of late activation may be dependent on the region on the map. In some embodiments, "late" may be considered to be about 10 milliseconds later than all the points surrounding the specific map region under consideration. With regards to the given threshold for identifying peaks, the threshold may be set to any suitable level, for example, 10 micro-Volts.

The mapping system then finds the signal segments not conforming to the signal characteristic(s) for the given time period and saves non-conforming signal segments to a memory for future retrieval and inspection by the physician. The non-conforming signal segments may be saved with metadata such as the electrode which captured the signal segment, the time of capture, and optionally the nature of the non-conformity (e.g., late activation, double activation etc.). The mapping system may then render an indication to a display indicating that an electrode captured the non-conforming signal segment optionally with an identification of the capturing electrode.

In some embodiments, the indication may be implemented by highlighting or otherwise coloring or shading the relevant electrode on a representation of the catheter. In some embodiments, the indication remains visible until removed by the physician.

In other embodiments, the indication may be removed automatically after a time-out (e.g., within a cardiac cycle). If the same electrode is still capturing a non-conforming signal segment for the next time period, the indication is rendered again. In this manner if the non-conforming signal segment is a one-off occurrence (or repeating a few times for example) e.g., due to noise, the indication will disappear, whereas if the non-conforming signal segment is repetitive (e.g., due to a physiological effect) then the indication will flash on and off repetitively thereby alerting the physician that a non-conforming signal segment has been captured. The physician may then request rendering of the non-conforming signal segment on the display for inspection.

System Description

Reference is now made to FIG. 1, which is a schematic, pictorial illustration of a catheter tracking system 20, in accordance with an embodiment of the present invention. The system 20 includes a catheter 40 configured to be inserted into a body part (e.g., a chamber of a heart 26) of a living subject (e.g., a patient 28). A physician 30 navigates the catheter 40 (for example, a basket catheter produced by Biosense Webster, Inc. of Irvine, CA, USA), seen in detail in inset 45, to a target location in the heart 26 of the patient 28, by manipulating a deflectable segment of an insertion tube 22 of the catheter 40, using a manipulator 32 near a proximal end 29 of the insertion tube 22, and/or deflection from a sheath 23. In the pictured embodiment, physician 30 uses catheter 40 to perform electro-anatomical mapping of a cardiac chamber.

The catheter 40 includes a distal end 33. The distal end 33 of the catheter 40 includes an assembly 35 (e.g., a basket assembly as shown in FIG. 1 or a balloon assembly or any suitable distal end assembly, e.g., grid, flexible splines or a focal catheter) on which at least one (e.g., multiple) catheter electrode(s) 48 (only some labeled for the sake of simplicity) are disposed. The electrodes 48 are configured to contact tissue at respective locations with the chamber of the heart. The assembly 35 is disposed distally to the insertion tube 22 and may be connected to the insertion tube 22 via a coupling member of the insertion tube 22 at the distal end 33. The coupling member of the insertion tube 22 may be formed as an integral part of the rest of the insertion tube 22 or as a separate element which connects with the rest of the insertion tube 22.

The assembly 35 further comprises multiple flexible strips 55 (only two labeled for the sake of simplicity), to each of which are coupled the electrodes 48. The assembly 35 may include any suitable number of electrodes 48. In some embodiments, the assembly 35 may include ten flexible strips 55 and 120 electrodes, with twelve electrodes disposed on each flexible strip 55.

The catheter 40 includes a pusher 37. The pusher 37 is typically a tube that is disposed in a lumen of the insertion tube 22 and spans from the proximal end 29 to the distal end 33 of the insertion tube 22. A distal end of the pusher 37 is connected to distal ends of the flexible strips 55, typically via a coupling member of the pusher 37. The coupling member of the pusher 37 may be formed as an integral part of the rest of the pusher 37 or as a separate element which connects with the rest of the pusher 37. The distal end of the insertion tube 22 is connected to proximal ends of the flexible strips 55, typically via the coupling member of the distal end 33. The pusher 37 is generally controlled via the manipulator 32 to deploy the assembly 35 and change an ellipticity of the assembly 35 according to the longitudinal displacement of the pusher 37 with respect to the insertion tube 22. The actual basket assembly 35 structure may vary. For example, flexible strips 55 may be made of a printed circuit board (PCB), or of a shape-memory alloy, or any suitable material.

Embodiments described herein refer mainly to a basket distal-end assembly 35, purely by way of example. In alternative embodiments, the disclosed techniques can be used with a catheter having a balloon-based distal-end assembly or of any other suitable type of distal-end assembly.

Catheter 40 is inserted in a folded configuration, through sheath 23, and only after the catheter 40 exits sheath 23 is catheter 40 able to change shape by retracting pusher 37. By containing catheter 40 in a folded configuration, sheath 23 also serves to minimize vascular trauma on its way to the target location.

The distal end 33 of the catheter 40 comprises magnetic coil sensors 50A and 50B. The magnetic coil sensor 50A is shown in inset 45 at the distal edge of insertion tube 22 (i.e., at the proximal edge of basket assembly 35). The sensor 50A may be a Single-Axis Sensor (SAS), or a Double-Axis Sensor (DAS) or a Triple-Axis Sensor (TAS). Similarly, the sensor 50B may be a SAS, DAS, or TAS. Magnetic coil sensors 50A and 50B and electrodes 48 are connected by wires running through insertion tube 22 to various driver circuitries in a console 24.

In some embodiments, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance between sensors 50A and 50B. Patient 28 is placed in a magnetic field generated by a pad containing multiple magnetic field generator coils 42, which are driven by a unit 43. The magnetic field generator coils 42 are configured to generate respective alternating magnetic fields, having respective different frequencies, into a region where a body-part (e.g., the heart 26) of a living subject (e.g., the patient 28) is located. The magnetic coil sensors 50A and 50B are configured to output electrical signals responsively to detecting the respective magnetic fields. For example, if there are nine magnetic field generator coils 42 generating nine respective different alternating magnetic fields with nine respective different frequencies, the electrical signals output by the magnetic coil sensors 50 will include components of the nine different frequency alternating magnetic fields. The magnitude of each of the magnetic fields varies with distance from the respective magnetic field generator coils 42 such that the location of the magnetic coil sensors 50 may be determined from the magnetic fields sensed by the magnetic coil sensors 50. Therefore, the transmitted alternating magnetic fields generate the electrical signals in sensors 50A and 50B, so that the electrical signals are indicative of position and orientation of the magnetic coil sensors 50.

The generated signals are transmitted to console 24 and become corresponding electrical inputs to processing circuitry 41. The processing circuitry 41 may use the signals to compute: the elongation of the basket assembly 35, in order to estimate basket ellipticity and elongation/retraction state from the calculated distance between sensors 50A and 50B; and compute a relative orientation between the axes of the sensors 50A and 50B to estimate a shape of the expandable distal end assembly 35 (e.g., a basket shape) responsively to the relative orientation, as described in more detail below.

The bow of the flexible strips 55 and/or the positions of the electrodes 48 (or other features) on the flexible strips 55 with respect to a fixed point on the catheter 40 (such as the distal tip of the insertion tube 22) may be measured for various distances between the magnetic sensors 50A, 50B and for various relative orientation angles between the magnetic sensors 50A, 50B. For example, the positions of the electrodes 48 with respect to the fixed point on the catheter 40 may be measured for every 0.2 mm movement of the pusher 37 with respect to the insertion tube 22 and for every 1 degree of relative orientation between the magnetic sensors 50A, 50B (up to a maximum sideways movement of the assembly 35). At each different distance/relative-orientation combination, the computed distance and computed relative orientation angle between the magnetic sensors 50A, 50B is recorded along with the position data of the electrodes 48. This data may then be used to estimate the bow of the flexible strips 55 and/or the positions of the electrodes 48 (or other features) on the flexible strips 55 with respect to a fixed point on the catheter 40 (such as the distal tip of the insertion tube 22) responsively to the computed distance and relative orientation angle between the magnetic sensors 50A, 50B.

Additionally, or alternatively, the bow of the flexible strips 55 may be estimated based on the following assumptions: (a) each of the flexible strips 55 is of a fixed and known length; (b) each of the flexible strips 55 is connected to the pusher 37 via a coupler, with the distal ends of the flexible strips 55 being substantially perpendicular (within an error of plus or minus 10 degrees) to the longitudinal axis of the insertion tube 22; (c) each of the flexible strips 55 is connected to the insertion tube 22 via a coupler, which couples the proximal ends of the flexible strips 55 to the insertion tube 22, substantially parallel (within an error of plus or minus 10 degrees) to the longitudinal axis of the insertion tube 22. Based on the above assumptions (a)-(c), and the computed positions of the couplers based on the computed positions of the magnetic sensors 50A, 50B, the bow of each of the flexible strips 55 may be computed using a third-degree polynomial. In some embodiments, the bow of the flexible strips 55 and/or the positions of the electrodes 48 (or other features) on the flexible strips 55 with respect to a fixed point on the catheter 40 (such as the distal tip of the insertion tube 22) may be computed based on the computed distance and orientation between the magnetic sensors 50A, 50B and a model of the catheter 40 which provides the bow of the flexible strips 55 and/or the positions of the electrodes 48 for the computed distance based on the mechanical properties and dimensions of the flexible strips 55.

A method of position and/or direction sensing using external magnetic fields and magnetic coil sensors, such as sensors 50A and 50B, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1.

In some embodiments, the processing circuitry 41 uses position-signals received from the electrodes 48 or body surface electrodes 49, and the magnetic sensor 50 to estimate a position of the assembly 35 inside a body part, such as inside a cardiac chamber. In some embodiments, the processing circuitry 41 correlates the position signals received from the electrodes 48, 49 with previously acquired magnetic location-calibrated position signals, to estimate the position of the assembly 35 inside the body part. The position coordinates of the electrodes 48 may be determined by the processing circuitry 41 based on, among other inputs, measured impedances, voltages or on proportions of currents distribution, between the electrodes 48 and the body surface electrodes 49.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1.

The Carto® 3 system applies Active Current Location (ACL) which is a hybrid current-distribution and magnetic-based position-tracking technology. In some embodiments, using ACL, the processing circuitry 41 estimates the positions of the electrodes 48. In some embodiments, the signals received from the electrodes 48, 49 are correlated with a current-to-position matrix (CPM) which maps current distribution ratios (or another electrical value) with a position that was previously acquired from magnetic location-calibrated position signals. The current distribution ratios are based on measurements of the body surface electrodes 49 of current flowing from the electrodes 48 to the body surface electrodes 49.

In some embodiments, to visualize catheters which do not include a magnetic sensor, the processing circuitry 41 may apply an electrical signal-based method, referred to as Independent Current Location (ICL) technology. In ICL, the processing circuitry 41 calculates a local scaling factor for each voxel of the volume in which catheters are visualized. The factor is determined using a catheter with multiple electrodes having a known spatial relationship, such as a lasso-shaped catheter. However, although yielding accurate local scaling (e.g., over several millimeters), ICL is less accurate when applied to a volume of a whole heart chamber, whose size is in the order of centimeters. The ICL method, in which positions are calculated based on current distribution proportions can have errors and may yield a distorted shape of the assembly 35, due to the non-linear nature of the current-based ICL space. In some embodiments, the processing circuitry 41 may apply the disclosed ICL method to scale ICL space and the assembly 35 shape into a correct one, based on known smaller scale distances between electrodes of a lasso-shaped catheter, for example, as well as based on larger scale distances, themselves based on the known distance between the electrodes 48 at the ends of the assembly 35.

Processing circuitry 41, typically part of a general-purpose computer, is further connected via a suitable front end and interface circuits 44, to receive signals from body surface-electrodes 49. Processing circuitry 41 is connected to surface-electrodes 49 by wires running through a cable 39 to the chest of patient 28. The catheter 40 includes a connector 47 disposed at the proximal end 29 of the insertion tube 22 for coupling to the processing circuitry 41.

In some embodiments, processing circuitry 41 renders to a display 27, a representation 31 of at least a part of the catheter 40 and a body-part, (e.g., from a mapping process or from a scan (e.g., CT or MRI) of the body-part previously registered with the system 20), responsively to computed position coordinates of the insertion tube 22 and the flexible strips 55.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. The system 20 may also include a memory 51 used by the processing circuitry 41.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Figure 2:
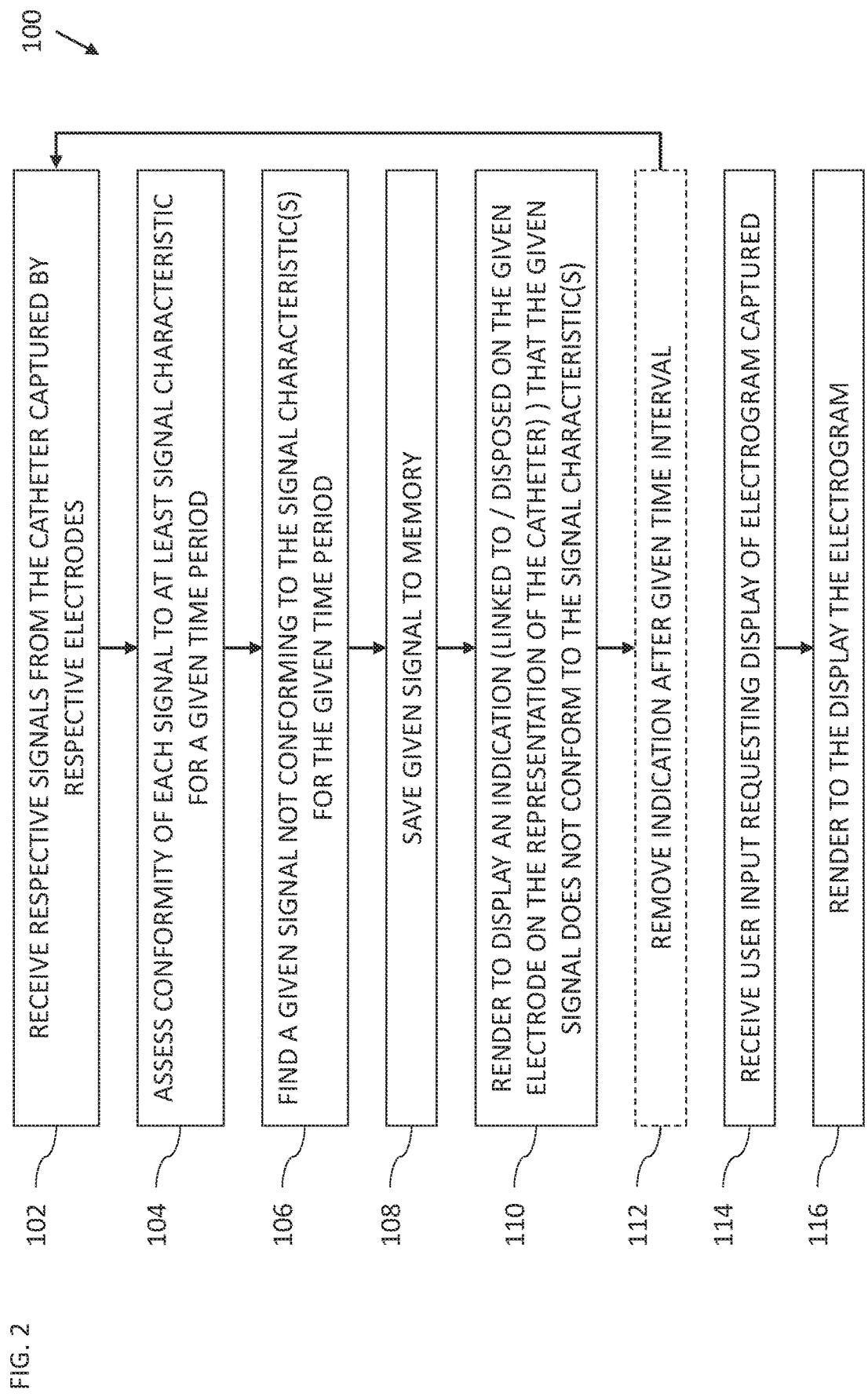
FIG. 2 is a flowchart including steps in a method of operation of the system of FIG. 1.

Reference is now made to FIG. 2, which is a flowchart 100 including steps in a method of operation of the system 20 of FIG. 1. Reference is also made to FIG. 1.

The processing circuitry 41 is configured to receive respective signals from the catheter 40 captured by respective ones of the electrodes 48 (block 102). The processing circuitry 41 is configured to assess conformity of each of the respective signals to at least one signal characteristic for a given time period (block 104). The signal characteristic for a given time period may be a predetermined signal characteristic that is used for comparative purposes with the signals recorded by the electrodes.

The "given time period" may include a complete cardiac cycle, multiple cardiac cycles, a predefined time interval within a cardiac cycle, any time intervals that may include any portion of the P-wave, QRS complex or T-wave in one cardiac cycle or from one cardiac cycle to subsequent cardiac cycles. The given time period may be any suitable length. In some embodiments, the given time period is equal to a window of interest in current or most recent cardiac cycle. In other embodiments, the given time period is equal to multiple windows of interest of respective most recent cardiac cycles and therefore an indication (described in more detail below) is provided after several successive cardiac cycles of detecting non-conformity with the signal characteristics.

The signals (collected by the electrodes) for a given time period may also be referred to as signal segments for the given time period. The "signal characteristics" for classifying a collected or recorded signal segment (for a given time period) as a valid mapping signal may include a signal having a single activation early enough in the cardiac cycle. The term "single activation" is defined herein as a single peak below a given threshold. With regards to the given threshold for identifying peaks in the recorded signals or signal segments, the threshold may be set to any suitable level, for example, approximately 10 micro-Volts. Signal segments with late activation, double activation, multiple activation, or unclear activations may be excluded as not conforming with the signal characteristics. In some embodiments, peaks of the recorded signals or signal segments above a given threshold are considered as possible activations (i.e., signals considered to be in conformity for step 104), whereas peaks of the recorded signals or signal segments below the given threshold are not considered as possible activations (i.e., not conforming as in step 106) for determining how many activations a signal segment has in the window of interest and how late the activations are in the window of interest. The activation time of the measured or recorded signals may be defined by the steepest negative slope of a candidate peak or any other suitable criteria of the recorded signals or signal segments. The definition of "early enough" in the cardiac cycle, the window of interest, and the given threshold for identifying peaks may be implementation specific and/or physician defined. In some embodiments, the physician defines the "window of interest". For example, in atrial procedures, the "window of interest" may be defined by setting limits around the P wave, which may be identified based on the R peak of the QRS complex. The definition of late activation may be dependent on the region on the map. In some embodiments, "late" may be considered to be about 10 milliseconds later than all the points surrounding the specific map region under consideration. With regards to the given threshold for identifying peaks in the recorded signals or signal segments, the threshold may be set to any suitable level, for example, approximately 10 micro-Volts.

The processing circuitry 41 is configured to find a given one of the signals (e.g., signal segment) of a given one of the electrodes 48 not conforming to the signal characteristic(s) for the given (current or most recent) time period (block 106). It may happen that more than one of the recorded signals of more than one corresponding electrode 48 may not conform to the pre-defined signal characteristic(s) for the given time period. The processing circuitry 41 is configured to save the given signal (which may be non-conforming or non-standard) to the memory 51 for future rendering to the display 27 (block 108).

Figure 3:
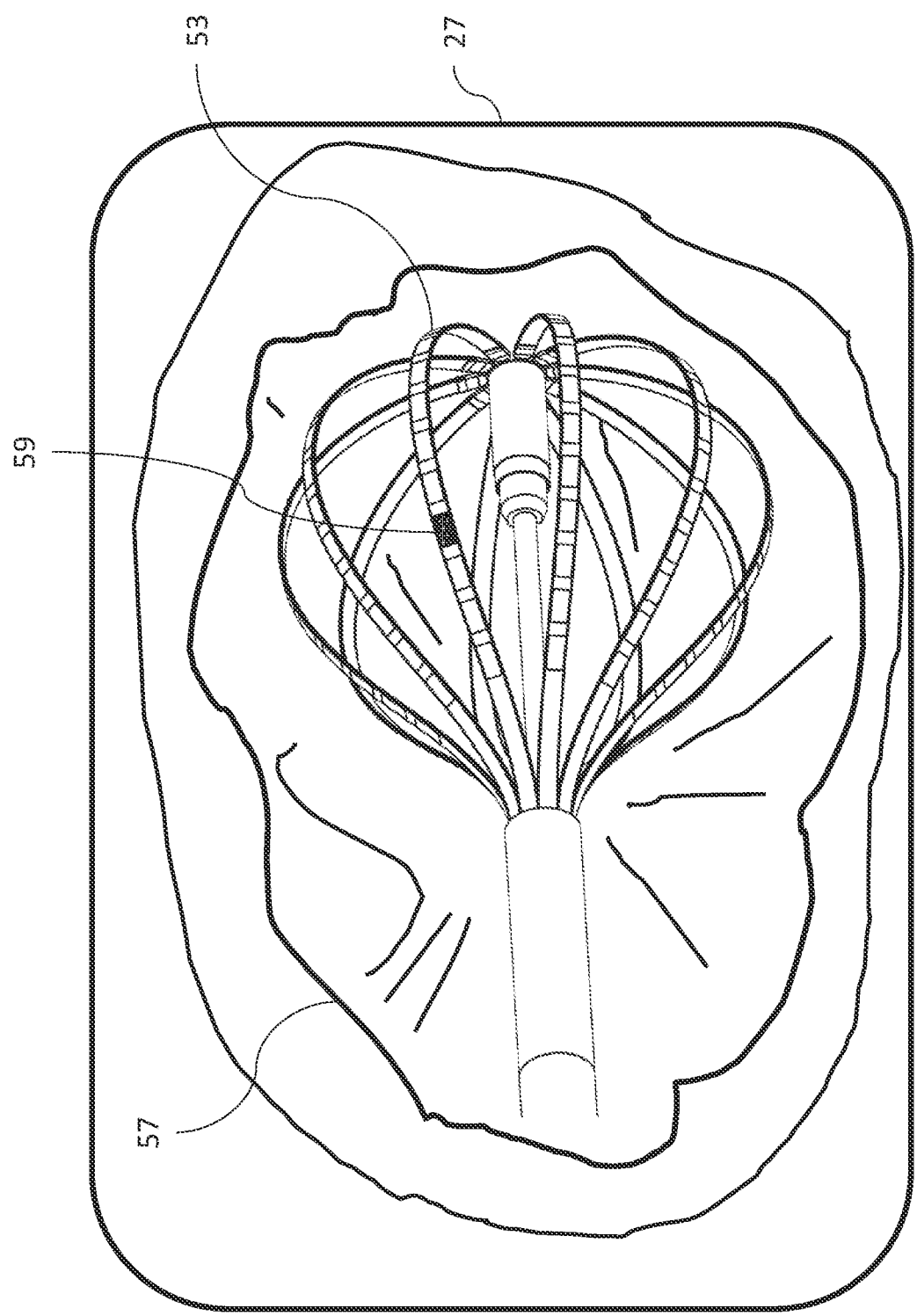
FIG. 3 is a schematic view of a representation of a catheter in an anatomical map with an indication of an electrode capturing a non-standard signal rendered in the system of FIG. 1.

Reference is now made to FIG. 3, which is a schematic view of a representation 53 of the catheter 40 in an anatomical map 57 with an indication 59 that least one of the electrodes 48 is capturing (or captured) a non-standard signal rendered in the system 20 of FIG. 1. Reference is also made to FIG. 2.

The processing circuitry 41 is configured to render to the display 27 the indication 59 that the given signal of the given electrode 48 does not conform to the signal characteristic(s) for the given time period (block 110). The indication 59 may include rendering the identification (e.g., electrode number(s) and/or letter(s)) of the given electrode 48 on the display 27 with an optional explanation that the given electrode 48 captured a non-conforming signal (not shown in FIG. 3).

In some embodiments, the processing circuitry 41 is configured to render to the display 27 the representation 53 of the catheter 40 with the indication 59 that the given signal of the given electrode 48 does not conform to the signal characteristic(s) for the given time period, wherein the indication 59 is linked to the given electrode 48 on the representation 53 of the catheter 40, for example, by pointing to the given electrode with an arrow (not shown in FIG. 3).

In some embodiments, the processing circuitry 41 is configured to render to the display 27 the representation 53 of the catheter 40 with the indication 59 that the given signal of the given electrode 48 does not conform to the signal characteristic(s) for the given time period, wherein the indication 59 is disposed on the given electrode 48 on the representation 53 of the catheter 40 as shown in FIG. 3. The indication 59 may be any suitable color and/or shading and/or pattern and/or a border around the given electrode on the representation 53.

In some embodiments, the indication 59 is rendered until a request is received from the physician 30 to remove the indication 59. In other embodiments, the processing circuitry 41 is configured to render to the display 27 the indication 59 disposed on the given electrode 48 on the representation 53 of the catheter 40 for a given time interval (for example, equal to a duration about the length of the given time period). The processing circuitry 41 is configured to remove the indication 59 from the given electrode 48 on the representation 53 of the catheter 40 (after expiration of the given time interval). The steps of blocks 102-110 are repeated for a subsequent time period, which may lead to the processing circuitry 41 repeating rendering to the display 27 the indication 59 disposed on the given electrode 48 on the representation 53 of the catheter 40 responsively to finding that the given signal of the given electrode 48 does not conform to the signal characteristic(s) for the subsequent time period. The steps of blocks 102-112 are repeated for more time periods and different electrodes may be found to be capturing signal segments not conforming to the signal characteristic(s).

In some embodiments, the processing circuitry 41 is configured to render to the display 27 the indication 59 disposed on the given electrode 48 on the representation 53 of the catheter 40 so that the indication 59 repeatedly flashes on and off responsively to multiple detections of the given signal of the given electrode 48 not conforming to the signal characteristic(s) for respective subsequent time periods. In some embodiments, the respective subsequent time periods correspond to respective windows of interest of respective cardiac cycles (i.e., each subsequent time period corresponds to a window of interest in a cardiac cycle). In this manner, the physician 30 may observe the flashing on and off of the indication 59, and if the flashing continues long enough (as determined by the physician 30), the physician 30 may realize that the signal being captured by the given electrode 48 is not just capturing an occasional noisy signal but is probably capturing a complex signal that should be displayed and examined in more detail.

Figure 4:
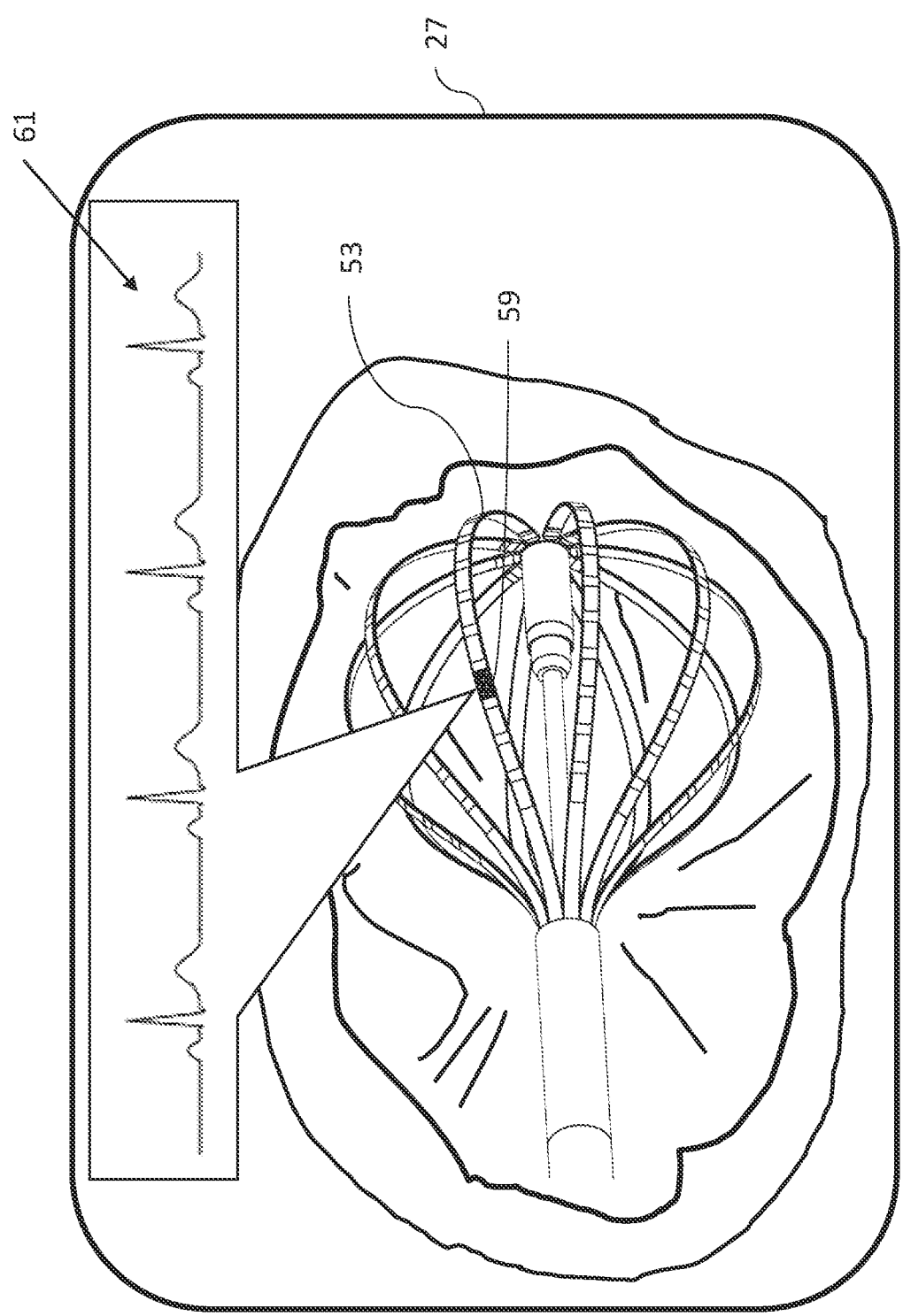
FIG. 4 is a schematic view of the representation of the catheter of FIG. 3 with an electrogram.

Reference is now made to FIG. 4, which is a schematic view of the representation 53 of the catheter 40 of FIG. 3 with an electrogram 61. Reference is also made to FIG. 2. In response to seeing the indication 59 (e.g., the indication 59 flashing on and off), the physician 30 may request the electrogram 61 to be displayed. The processing circuitry 41 is configured to receive a user input (from the physician 30) requesting display of the electrogram 61 captured by the given electrode 48 (block 114). The processing circuitry 41 is configured to render to the display 27 the electrogram 61 captured by the given electrode (block 116).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical system, comprising:
    a catheter configured to be inserted into a chamber of a heart of a living subject, and including catheter electrodes configured to contact tissue at respective locations within the chamber of the heart;
    a display; and
    a processing circuitry configured to:
        receive respective signals from the catheter captured by respective ones of the electrodes;
        assess conformity of each of the respective signals to at least one signal characteristic by classifying each signal as one of (i) a valid mapping signal that conforms to the at least one signal characteristic or (ii) a non-mapping signal that does not conform to the at least one signal characteristic;

find a given one of the signals of a given one of the electrodes not conforming to the at least one signal characteristic for a given time period;
render to the display an indication that the given one of the signals of the given one of the electrodes does not conform to the at least one signal characteristic for the given time period; and
render to the display a representation of the catheter with the indication that the given one of the signals of the given one of the electrodes does not conform to the at least one signal characteristic for the given time period, the indication being at least one of (i) linked to the given one of the electrodes on the representation of the catheter or (ii) disposed on the given one of the electrodes on the representation of the catheter.

2. The system according to claim 1, wherein the processing circuitry is configured to:
render to the display the indication disposed on the given one of the electrodes on the representation of the catheter for a given time interval;
remove the indication from the given one of the electrodes on the representation of the catheter; and
repeat rendering to the display of the indication disposed on the given one of the electrodes on the representation of the catheter responsively to finding that the given one of the signals of the given one of the electrodes does not conform to the at least one signal characteristic for a subsequent time period.

3. The system according to claim 2, wherein the processing circuitry is configured to render to the display the indication disposed on the given one of the electrodes on the representation of the catheter so that the indication repeatedly flashes on and off responsively to multiple detections of the given one of the signals of the given one of the electrodes not conforming to the at least one signal characteristic for respective subsequent time periods.

4. The system according to claim 3, wherein the respective subsequent time periods correspond to respective windows of interest of respective cardiac cycles.

5. The system according to claim 1, wherein the processing circuitry is configured to, following the rendering of the indication:
receive a user input requesting display of an electrogram captured by the given one of the electrodes; and
render to the display the electrogram captured by the given one of the electrodes.

6. The system according to claim 1, wherein the given one of the signals of the given one of the electrodes as being not conforming to the at least one signal characteristic include at least one signal segment with late activation, double activation, multiple activation, or unclear activations are excluded as not conforming to the at least one signal characteristic.

7. The system according to claim 1, wherein the given time period is equal to a window of interest in one cardiac cycle.

8. The system according to claim 1, wherein the given time period is equal to multiple windows of interest of respective cardiac cycles.

9. The system according to claim 1, wherein the processing circuitry is configured to save the given one of the signals to a memory for future rendering to the display.

10. A medical method, comprising:
receiving respective signals from a catheter inserted into a chamber of a heart of a living subject captured by respective electrodes of the catheter contacting tissue at respective locations within the chamber of the heart;
assessing conformity of each of the respective signals to at least one signal characteristic by classifying each signal as one of (i) a valid mapping signal that conforms to the at least one signal characteristic or (ii) a non-mapping signal that does not conform to the at least one signal characteristic;
finding a given one of the signals of a given one of the electrodes not conforming to the at least one signal characteristic for a given time period;
rendering to a display an indication that the given one of the signals of the given one of the electrodes does not conform to the at least one signal characteristic for the given time period; and
rendering to the display a representation of the catheter with the indication that the given one of the signals of the given one of the electrodes does not conform to the at least one signal characteristic for the given time period, the indication being at least one of (i) linked to the given one of the electrodes on the representation of the catheter or (ii) disposed on the given one of the electrodes on the representation of the catheter.

11. The method according to claim 10, wherein the rendering includes rendering to the display the indication disposed on the given one of the electrodes on the representation of the catheter for a given time interval, the method further comprising:
removing the indication from the given one of the electrodes on the representation of the catheter; and
repeating rendering to the display of the indication disposed on the given one of the electrodes on the representation of the catheter responsively to finding that the given one of the signals of the given one of the electrodes does not conform to the at least one signal characteristic for a subsequent time period.

12. The method according to claim 11, wherein the rendering includes rendering to the display the indication disposed on the given one of the electrodes on the representation of the catheter so that the indication repeatedly flashes on and off responsively to multiple detections of the given one of the signals of the given one of the electrodes not conforming to the at least one signal characteristic for respective subsequent time periods.

13. The method according to claim 12, wherein the respective subsequent time periods correspond to respective windows of interest of respective cardiac cycles.

14. The method according to claim 10, further comprising, following the rendering of the indication, receiving a user input requesting display of an electrogram captured by the given one of the electrodes, and wherein the rendering includes rendering to the display the electrogram captured by the given one of the electrodes.

15. The method according to claim 10, wherein the given time period is equal to a window of interest in one cardiac cycle.

16. The method according to claim 10, wherein the given time period is equal to multiple windows of interest of respective cardiac cycles.

17. The method according to claim 10, further comprising saving the given one of the signals to a memory for future rendering to the display.

18. A software product, comprising a non-transient computer-readable medium in which program instructions are stored, which instructions, when read by a central processing unit (CPU), cause the CPU to:

receive respective signals from a catheter inserted into a chamber of a heart of a living subject captured by respective electrodes of the catheter contacting tissue at respective locations within the chamber of the heart;

assess conformity of each of the respective signals to at least one signal characteristic by classifying each signal as one of (i) a valid mapping signal that conforms to the at least one signal characteristic or (ii) a non-mapping signal that does not conform to the at least one signal characteristic;

find a given one of the signals of a given one of the electrodes not conforming to the at least one signal characteristic for a given time period;

render to a display an indication that the given one of the signals of the given one of the electrodes does not conform to the at least one signal characteristic for the given time period; and render to the display a representation of the catheter with the indication that the given one of the signals of the given one of the electrodes does not conform to the at least one signal characteristic for the given time period, the indication being at least one of (i) linked to the given one of the electrodes on the representation of the catheter or (ii) disposed on the given one of the electrodes on the representation of the catheter.

* * * * *